(12) United States Patent
Piorkowski et al.

(10) Patent No.: US 7,234,812 B2
(45) Date of Patent: Jun. 26, 2007

(54) METHOD AND APPARATUS FOR MANUFACTURING A CUSTOM FIT OPTICAL DISPLAY HELMET

(75) Inventors: Gary J. Piorkowski, Mayfield, PA (US); William Radzelovage, Newton, NJ (US)

(73) Assignee: Crew Systems Corporation, Carbondale, PA (US)

( * ) Notice: Subject to any disclaimer, the term of this patent is extended or adjusted under 35 U.S.C. 154(b) by 674 days.

(21) Appl. No.: 10/788,052

(22) Filed: Feb. 25, 2004

(65) Prior Publication Data

US 2004/0163228 A1    Aug. 26, 2004

Related U.S. Application Data

(60) Provisional application No. 60/449,782, filed on Feb. 25, 2003.

(51) Int. Cl.
*A61B 3/00* (2006.01)
*A61B 3/14* (2006.01)
*A61B 3/02* (2006.01)
*G01D 21/00* (2006.01)
*B29C 65/00* (2006.01)

(52) U.S. Cl. ............ 351/200; 351/206; 351/209; 351/210; 351/240; 33/645; 33/512; 264/46.5; 2/410; 2/416; 2/417

(58) Field of Classification Search ........... 351/200, 351/206, 209–211, 240, 245; 33/512, 533, 33/613, 645; 264/46.5, 222; 2/6.3, 410, 2/416–419; 382/103, 128, 171; 348/51, 348/52, 78; 29/407.04, 720; 73/865.6; 600/558; 359/466, 409

See application file for complete search history.

(56) References Cited

U.S. PATENT DOCUMENTS

| 5,481,622 | A | * | 1/1996 | Gerhardt et al. ............ 382/103 |
|---|---|---|---|---|
| 5,584,073 | A | | 12/1996 | Radzelovage et al. |
| 5,604,818 | A | * | 2/1997 | Saitou et al. ............... 382/128 |
| 5,866,826 | A | | 2/1999 | Bataiole |
| 5,891,372 | A | | 4/1999 | Besset et al. |
| 6,279,172 | B1 | | 8/2001 | Epperson et al. |
| 6,487,786 | B2 | | 12/2002 | Beautz |
| 6,752,498 | B2 | * | 6/2004 | Covannon et al. .......... 351/240 |
| 2005/0099601 | A1 | * | 5/2005 | MacDougall et al. ....... 351/209 |

* cited by examiner

*Primary Examiner*—Loha Ben
(74) *Attorney, Agent, or Firm*—Cohen Pontani Lieberman & Pavane LLP

(57) ABSTRACT

A helmet with an optical display system is provided with a custom fit protective liner which precisely aligns the wearer's eyes with the optics on the helmet. The helmet is manufactured by positioning the subject's head in a fixture; determining the position of the subject's pupils with respect to the fixture; scanning the subject's head with a laser while positioned in the fixture in order to obtain a 3-D model of the subject's head; and providing a helmet liner having an outer surface which is profiled to position it inside a helmet shell. The position of the subject's pupils may be determined by scanning pupil locating features of the fixture. The 3-D model is then used to provide the helmet liner with an inner surface which conforms to the subject's head and is positioned with respect to the outer surface so that the outer surface will have a predetermined position with respect to the subject's pupils. The helmet liner is then fitted in the helmet shell to form a helmet. The helmet shell may thus be fitted with pre-positioned optics which are properly positioned with respect to the subject's pupils.

29 Claims, 4 Drawing Sheets

METHOD AND APPARATUS FOR MANUFACTURING A CUSTOM FIT OPTICAL DISPLAY HELMET

PRIORITY CLAIM

This application claims priority under 35 U.S.C. §119 from U.S. Provisional Application Ser. No. 60/449,782 which was filed on Feb. 25, 2003.

BACKGROUND OF THE INVENTION

1. Field of the Invention

The invention relates to a method for manufacturing a helmet, in particular for a pilot, wherein the helmet carries optics which must be precisely aligned with the pilot's eyes and must remain aligned when the helmet is subject to large forces. The invention also relates to an apparatus for determining the precise positioning of a subject's pupils with respect to a 3-D model of the subject's head.

2. Description of the Related Art

Optical display systems have added substantial mass to and adversely affected the center of gravity (CG) of typical flight helmets. At the same time, positioning and alignment of the optical system with respect to the user's eyes is very critical; the usable region of eye locus around the design position may be less than a 5 mm radius hemisphere.

The accurate eye-positioning requirement has generally been addressed by means of adjustable helmet fitting/suspension systems and/or adjustable optics. In either case, the added mass and adverse CG effects due to the optics leads to very large forces tending to shift the helmet location on the head during high-G aircraft maneuvers; the shift at +9 Gz is commonly great enough to cause total visual loss of the optical display.

It is accordingly very important not only that the helmet be precisely fitted to the pilot's head, but also that the optics be precisely fitted to the helmet so that it is precisely aligned with the pilots eyes and remains aligned when subjected to large forces.

Adjustable fitting/suspension systems may serve well as static eye positioning mechanisms. However, due to comfort-induced pressure limitations and the inability to eliminate vertical slack in the system (because of the relatively low weight of the helmet and optics at +1 Gz as compared to +9 Gz), vertical helmet motion due to the suspension tightening under the force of the 9-times increase in the helmet's weight at +9 Gz cannot be prevented.

U.S. Pat. No. 5,584,073 discloses a helmet system wherein the position of the helmet with respect to the wearer's head is adjusted to position the eyes where required. However system elasticity and concentrated pressure points contribute to helmet motion and therefore to difficulty in maintaining the position of the optics relative to the eyes under high loads.

U.S. Pat. No. 6,279,172 discloses a helmet system which reduces the aforementioned elasticity by using rigid plastic straps instead of nylon webbing, and reduces pressure in the brow region by using a poured foam forehead pad. However the performance was still less than ideal.

U.S. Pat. No. 6,487,786 discloses a method and a tool for aligning a helmet with respect to a wearer's head in the above described systems, but does not solve the problem of relative motion between the helmet and the wearer's head under high G forces.

Adjustable optics may assist in initial static fitting of the system to the wearer's eye locus, perhaps simplifying the fitting/suspension system. However, it cannot compensate for helmet movement under G-forces. Also, many current optical systems are not adjustable, for reasons of availablespace, complexity, mass, and tolerances inherent in adjustment systems.

U.S. Pat. No. 5,866,826 discloses a method which involves fitting the helmet to the pilot's head, determining the position of the subject's eyes with respect to the helmet by using an optical stand, and then fitting the optics to the helmet in accordance with the determined position using a jig to position the helmet so that the optics can be mounted using shims and the like. This results in a helmet which is virtually dedicated to a particular pilot, since both the lining and the optics are custom fitted.

SUMMARY OF THE INVENTION

It is a primary object of the invention to manufacture a helmet which is custom fit to a pilot's head in order to virtually eliminate relative motion between the helmet and the head even under high G forces.

It is a related object to position the pilot's eyes within the helmet so that the eyes are aligned with pre-positioned optics mounted on the helmet, so that only minimal (if any) adjustments to the optics are necessary.

It is a further object to provide an apparatus for determining the precise position of the subject's pupils with respect to a 3-D model of the subject's head, thereby facilitating manufacture of the helmet.

These objects are accomplishing by forming a custom fit protective liner (CFPL) which is custom manufactured for a particular pilot and fitted into a standard shell having pre-positioned optics. The CFPL combines successful 40-year old poured foam custom fit liner technology (using wax molds, plaster casts, and poured foaming chemicals) with the most modern methods available: laser scanning, CAD modeling, and CNC (computer numeric control) machining. The resulting CFPL is a fitting/suspension system optimized for optical display helmets that solves all of the performance problems evidenced by contemporary schemes, while also being well suited for use in standard helmets.

The CFPL is comprised of a rigid but crushable energy-absorbing (EA) material shaped such that its outside surface interfaces with and properly positions it within the inside of the helmet shell, and an inner surface that matches, with a constant offset, the shape of the wearer's head. This offset is filled by a thin layer of soft foam (the comfort layer) and a very thin against-the-head cover (such as leather). The surface formed by the cover is then an almost exact match to the wearer's head.

The inner head-matching surface of the CFPL is positioned with respect to the outer surface such that the wearer's eyes are located to within less than 2 mm of the location required by the optics, and the look angle is properly oriented, when the helmet is donned.

The vertical compliance of the CFPL is limited to less than the thickness of the comfort foam; the rest of the system is incompressible under normal operational loads. The CFPL is thusly capable of maintaining proper eye locus under maximally high Gz conditions.

The fact that the CFPL conforms to the shape of the head over a large surface area has other advantages. The pressure against the head is both uniform and minimum, eliminating so-called hot spots and maximizing comfort. Typical non-spherical head shapes provide great stability against rotational forces, and also allow a comfortable fit only with the head in the location built into the CFPL, assuring proper eye positioning. According to one embodiment of the method according to the invention, the CFPL is implemented by laser scanning the subject's head with eyes open (e.g. by using a Class 1 laser, which is safe for indefinite exposure) while wearing a thin close-fitting skull cap for hair compression. A marker indicating the subject's approximate preferred horizontal line of sight head orientation is included in the scan. The resulting 3-D head model is CAD-manipulated to add a small constant offset (a few mm) over the entire CFPL contact area to allow for the comfort foam and cover between the EA material and the head. This expanded head is subtracted from a CAD model of an EA component such that the head cutout is properly positioned with respect to the outer helmet-matching surface. A standard trim edge is adjusted if necessary for subject-specific earcup location needs. The result is a final EA liner CAD model that is transferred to CNC software for tool path generation and machining to final shape. This can be done from rectangular blocks of rigid EA foam, or from EA foam blanks molded such that the outer surface is near net shape to minimize machining time. Over predefined areas of the EA's outer surface material not required for impact protection is removed; this minimizes mass for heads smaller than the largest that will fit within that liner size. The comfort foam and cover are then added to the machined EA foam's inner surface, forming a complete CFPL.

The CFPL according to the invention offers numerous advantages over optical helmet fitting/suspension systems according to the prior art, including maximum comfort, maximum stability under both +Gz and rotational forces, minimum mass, and precise eye to optics positioning.

Further, the CFPL is adaptable to any helmet configuration, can easily incorporate ventilation features, and is readily adaptable to varying impact protection requirements by changing the EA material and or/the minimum thickness of the EA material.

In another embodiment of the method according to the invention, a laser is not used to directly determine the position of the eyes. This variation in the method results from three significant problems associated with laser scanning of the eyes:

(1) There is considerable variation in laser classification standards internationally, as well as much disagreement as to which classifications represent "eye-safe" lasers.

(2) Many pilots will refuse to be scanned with eyes open regardless of the laser classification.

(3) Because of the optical reflective characteristics of the eye, neither the corneal surface nor the pupil are defined in an eye-open scan with the precision and accuracy sufficient for an optimum CFPL.

To avoid these problems, the alternative method utilizes an apparatus that both positions the subject's head in a desired location and orientation, and provides precise eye location information by the position of readily identifiable features of the apparatus as they appear in the 3-D laser scans.

The apparatus according to the invention utilizes a fixture for positioning the subject's head and a pupil locating assembly having corneal locating blocks which can be precisely aligned with the subject's pupils. A 3-D model of the subject's skull can then be obtained by laser scanning the head, and the relative position of the eyes can be obtained by laser scanning orthogonal surfaces of the blocks while the eyes are closed or shielded.

The resulting 3-D CAD model of the head and components contains all needed information to properly manufacture a CFPL, since the location of the corneal surface at the pupil center is uniquely determined by the positions of the block surfaces in the model and their known distances in front, above, and outboard the pupil.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

DETAILED DESCRIPTION OF THE PRESENTLY PREFERRED EMBODIMENTS

Figure 1:
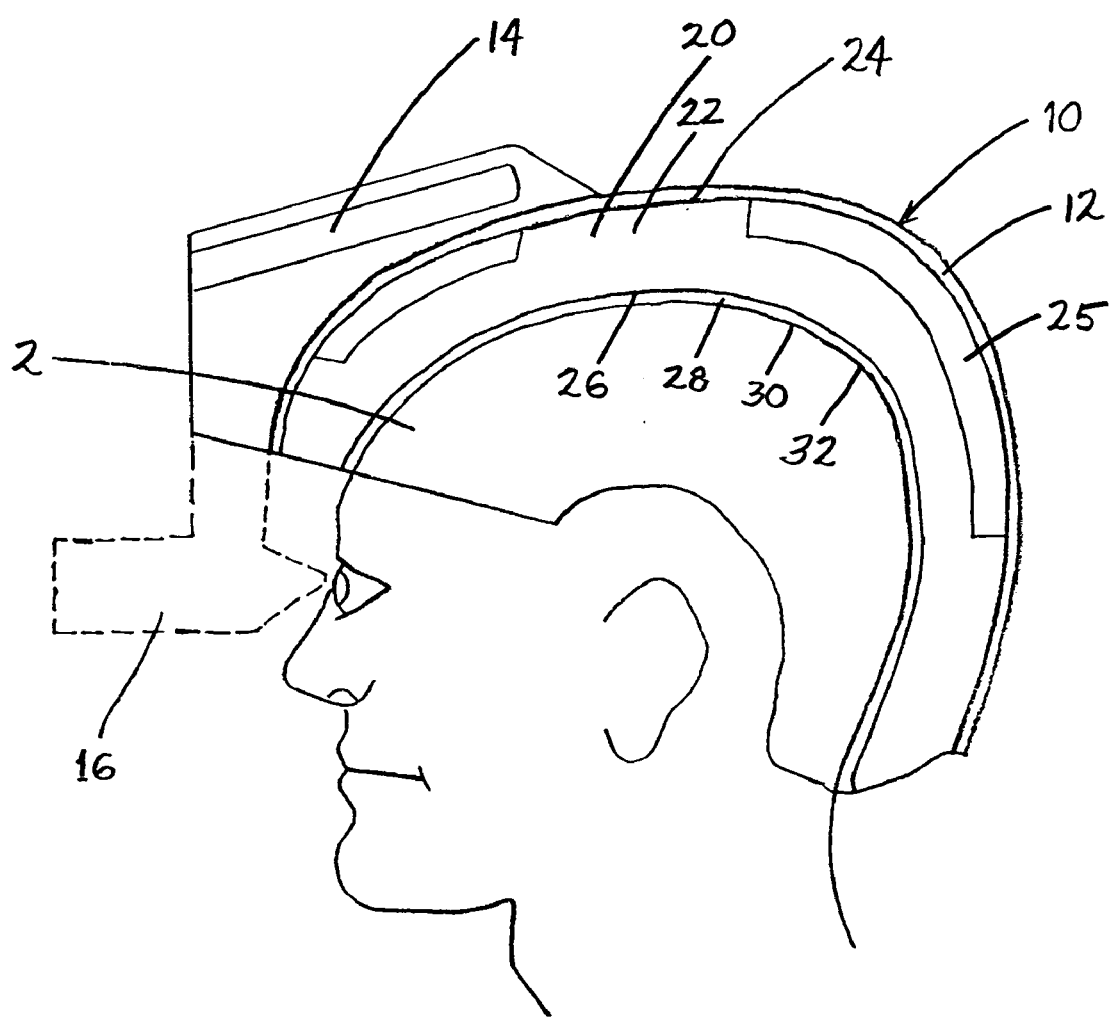
FIG. 1 is a schematic view of a subject's head inside a custom fitted helmet with an optical system mounted on the helmet.

FIG. 1 shows a subject's head 2 fitted with a helmet 10 comprising a helmet shell 12 provided with electronics and/or optics 14 for projecting an image onto a visor, or optics 16 which are aligned with the subject's eyes when the helmet 10 is in place. This alignment is achieved with a custom-fit protective liner 20 which brings the subjects eyes into alignment with and the proper distance from the visor image or the optics 16, without the need for adjusting the position of the optics with respect to the helmet shell 12.

The custom-fit protective liner 20 includes a block of energy absorbing material 22 having an outer surface 24 which forms the outer surface of the protective liner, and an inner surface 26 which is offset from the subject's head by a constant distance which is compensated by a layer of comfort foam 28 and a cover 30 having a collective thickness substantially equal to the offset. The cover 30 therefore has an inner surface 32 which forms the inner surface of the custom fit protective layer, so that the helmet conforms to the subject's head and permits very little play. The outer surface 24 of the energy absorbing material 22 is provided with slots 25 where material has been removed in areas where it is not needed in order to reduce the overall weight of the helmet.

The method of manufacturing the custom fit protective liner 20 will now be described in conjunction with the apparatus used to practice the method.

Figure 2:
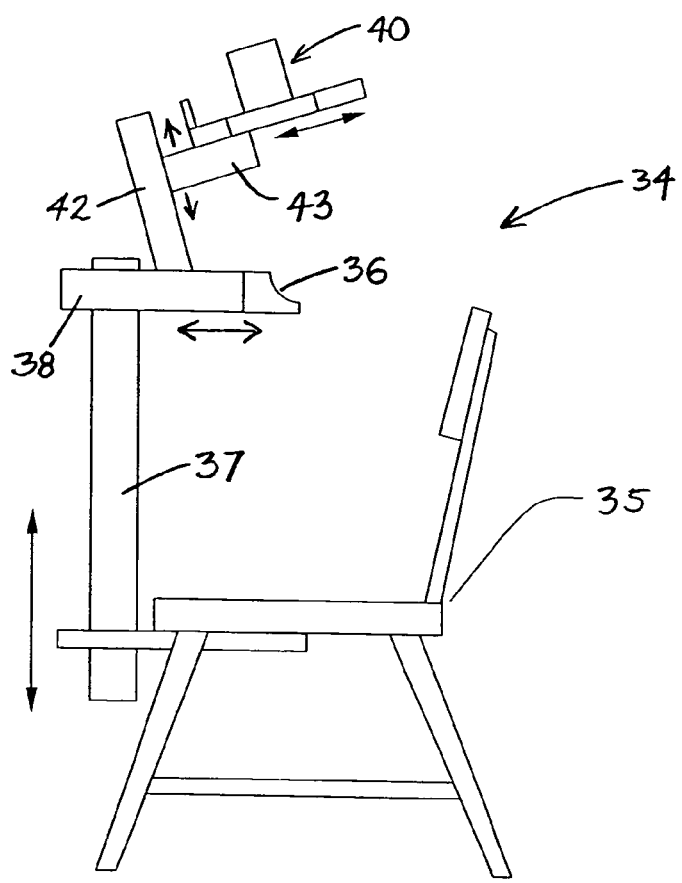
FIG. 2 is a schematic view of a fixture for positioning a subject's head, and a pupil locating assembly.

FIG. 2 shows a fixture 34 including a seat 35 and a chin support 36 whose position can be adjusted by means of a vertically movable post 37 and a horizontally movable beam 38. A pupil locating assembly 40 includes a central holding block 44 (FIG. 3) which is slideably received in a channel 43, which in turn is vertically movable on a post 42.

Figure 3:
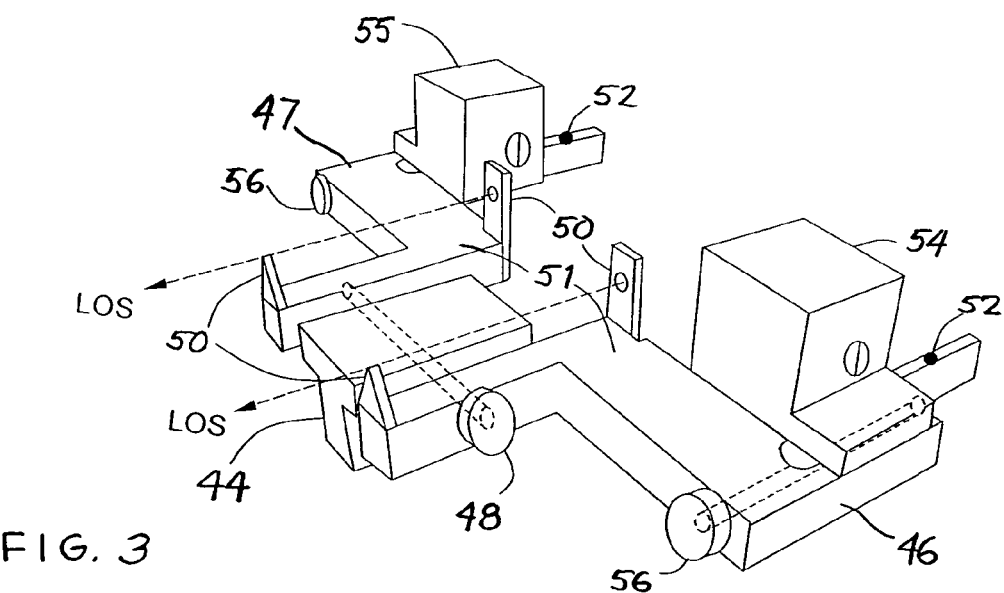
FIG. 3 is a schematic perspective view of the pupil locating assembly.

FIG. 3 shows the pupil locating assembly 40 in greater detail. Left and right sighting blocks 46, 47 are mounted for lateral movement with respect to central holding block 44, which has a T-shaped cross-section received in the channel 43. The blocks 46, 47 can be moved symmetrically toward or away from the holding block 44 by an adjusting screw 48. This is a special screw having a right hand thread in one of the sighting blocks, a left hand thread in the other sighting block, and an unthreaded shank portion which is axially positioned in the holding block 44. Each sighting block 46, 47 is provided with a sight 50 for aligning with respective pupils and establishing a line of sight at a fixed distance above reference surface 51 while the subject's head is resting on the chin support 36. The sights 50 may therefore be properly separated to match the interpupillary distance by turning the adjusting screw 48. The reference surfaces 51 have rear extensions provided with anthropometric aligning features 52 which can be used to properly orient the subject's head (in the nose up/nose down sense) during the scanning process. Left and right corneal locating blocks 54, 55 are mounted on respective sighting blocks 46, 47 for fore and aft movement, the position of each corneal locating block being adjusted by a respective adjusting screw 56.

Figure 4:
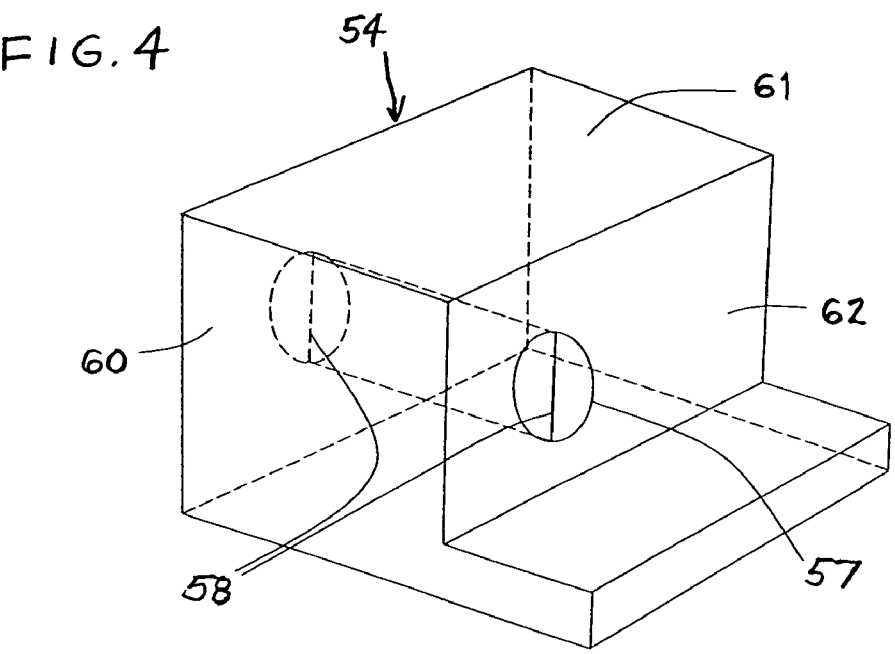
FIG. 4 is a perspective view of the left-side corneal locating block.

Referring to FIG. 4, corneal alignment is achieved by aligning the verticle reticules 58 with the foremost part of the subject's cornea by turning the screws 56 while sighting through the bore 57 containing the reticules. This is performed for each eye separately. Each block 54, 55 is provided with a forward surface 60, a top surface 61, and side surface 62 which can be scanned in order to provide a three dimensional image of the blocks. Since the bores 57 have axes which are parallel to the respective front surfaces 60 and top surfaces 61 at the same distance above the reference surface 51 as the line of sight as determined by the sights 50, and since the outer surface 62 is at a fixed distance from the line of sight (LOS), the scanning of blocks 54, 55 provides positional information which can be translated into the three dimensional position of the subject's pupils, including the interpupillary distance.

Figure 5:
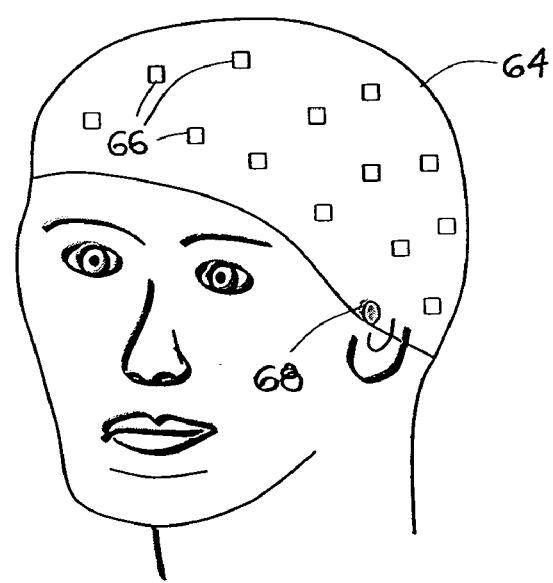
FIG. 5 is a view of the subject's head fitted with a skull cap.

FIG. 5 shows the subject's head fitted with a close-fitting skull cap 64 provided with markers 66 which are distributed substantially uniformly on the cap, and a pair of dots 68 which are aligned over anthropometric aligning features on the subject's head, for example the tragions. These dots 68 can then be aligned with the anthropometric features 52 on the sighting blocks 46, 47.

In order to perform a scan of the subject's head, the skull cap 64 is fitted as shown in FIG. 5, whereupon the subject is seated in the seat 35 shown in FIG. 2. The chin support 36 is then adjusted so that the subject's chin rests comfortably thereon. The pupil locating assembly 40 is positioned by moving the channel 43 vertically on the post 42, and the holding block 44 in the channel 43 so that the anthropometric aligning points 68 on the skull cap are aligned with the aligning features 52 on the sighting blocks 46, 47. The positions of the various parts may be fixed by set screws, pins, or other well known means. Before the positioning of the head in the fixture and the pupil locating assembly 40, the sighting blocks 46, 47 are adjusted to correspond to the lines of sight as determined by a pre-measured interpupillary distance. Finally, the corneal locating blocks 54, 55 are moved fore or aft as necessary so that the reticules 58 align with respective corneas.

Figure 6:
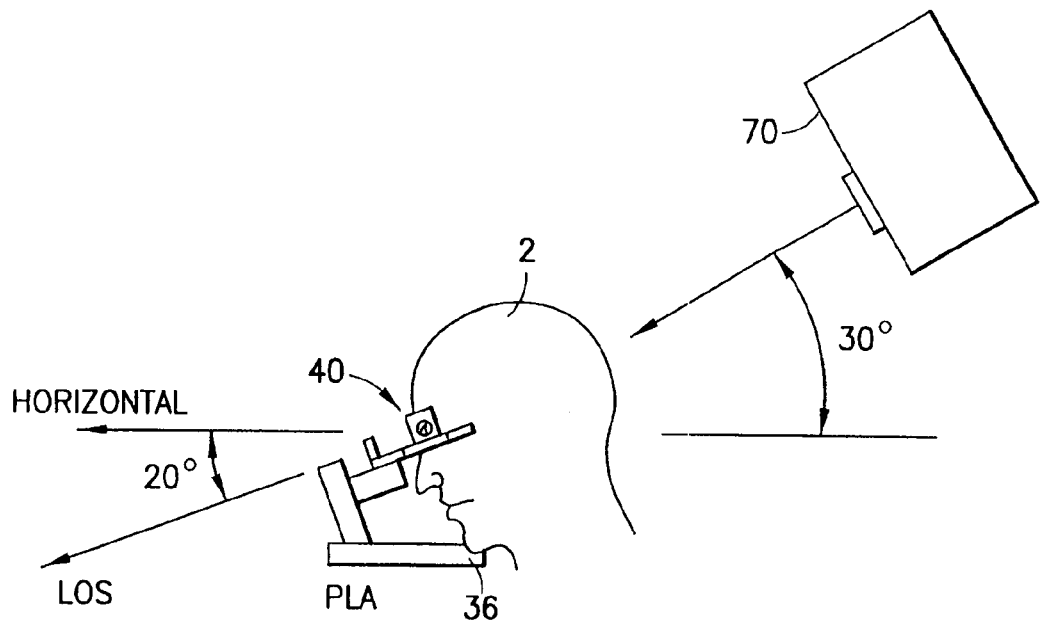
FIG. 6 is a side view of the camera orientation.

FIG. 6 shows the head 2 on chin support 36 with the pupil locating assembly 40 fully adjusted, as described above, so that the position of corneal locating blocks 54, 55 represents the position of the corneas, and therefore the pupils, including the interpupillary distance. The head is preferably oriented so that the line of sight (LOS) is twenty degrees downward from horizontal, which facilitates scanning the head with camera 70. The camera 70 is a laser scanning camera, for example a Minolta Vivid 910 laser scanning system, which is preferably oriented at thirty degrees to the horizontal as shown.

Figure 7:
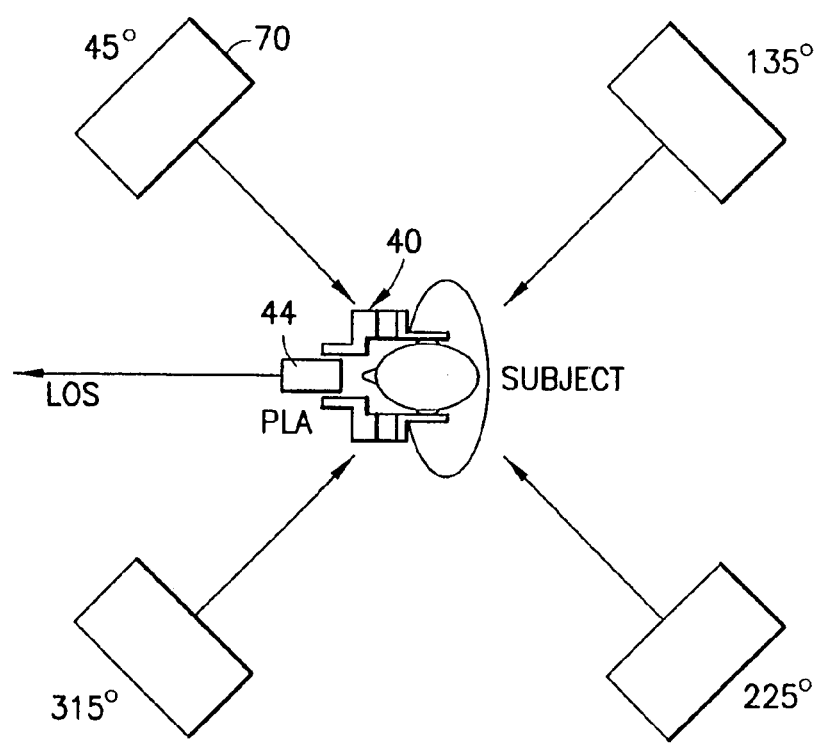
FIG. 7 is a plan view of the camera with respect to the subject as camera images are obtained.

FIG. 7 shows the camera 70 at four respective positions with respect to the subject's head, where it records 3-D images of the skull cap, and the corneal locating blocks 54, 55. At least one and preferably three markers 66 appear commonly in each adjacent pair of images, which permits computer merging of the images into an accurate 3-D model of the head. The images are preferably taken at 45°, 135°, 225°, and 315° with respect to the subject's line of sight. While different numbers of images and different angles are possible, it is important that the camera be located so that all three orthogonal surface 60, 61, 62 of each corneal locating block 54, 55 be visible in a respective image, so that the three dimensional position of the blocks 54, 55 can be accurately determined. During this process, the subject's eyes are in general not visible to the laser camera, and in any case need not be open during scanning.

FIG. 7 shows the camera 70 at different positions with respect to the subject's head and the pupil locating assembly 40. This positioning may be achieved by rotating the subject with respect to a fixed camera, rather than moving the camera around the subject. For example, the fixture 34 (FIG. 2) can be placed on a turntable, rather than providing a circular track for the camera.

The resulting complete 3-D CAD model of the head 2 and corneal locating blocks 54, 55 contains all the needed information to manufacture a custom fit protective liner 20 for helmet 10, since the location of the corneal surface at the pupil center is uniquely determined by the positions of surfaces 60, 61, 62 in the model, and their known distances in front of, above, and outboard from the pupils.

To provide the liner 20 with comfort foam 28 and a cover 30, as shown in FIG. 1, the 3-D CAD model of the head is manipulated to provide a constant offset (a few mm) over the entire CFPL contact area. This expanded head is subtracted from a CAD model of an energy absorbing component so that the head cut-out is properly positioned with respect to the outer surface of the energy absorbing material. That is, the inner surface is positioned so that optics fitted to the helmet in a standard position will be accurately aligned with the subject's eyes when the liner is fitted in a helmet shell and the helmet is worn by the subject for which the liner is custom fitted.

The result is a CAD model for an energy absorbing liner which is transferred to CNC software for tool path generation and machining to final shape. This can be done from rectangular blocks of rigid energy absorbing foam, or from foam blanks molded such that the outer surface is near net shape in order to minimize machining time. The foam material not required for impact protection may be removed from pre-defined areas of the outer surface, as indicated by slots 25 in FIG. 1, to minimize mass for heads smaller than the largest that will fit within the liner.

Thus, while there have been shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

What is claimed is:

1. A method of manufacturing a helmet with an optical display system, wherein the helmet is custom fitted to a subject's head, the method comprising:
   positioning the subject's head in a fixture;
   determining the position of the subject's pupils with respect to the fixture;
   scanning the subject's head with a laser while positioned in the fixture in order to obtain a 3-D model of the subject's head;
   providing a helmet liner having an outer surface which is profiled to position it inside a helmet shell;
   using the 3-D model to provide the helmet liner with an inner surface which conforms to the subject's head and is positioned with respect to the outer surface so that the outer surface will have a predetermined position with respect to the subject's pupils; and
   fitting the helmet liner in the helmet shell to form a helmet, whereby,
   the helmet shell may be fitted with pre-positioned optics which are properly positioned with respect to the subject's pupils when the helmet is worn on the subject's head.

2. A method as in claim 1 further comprising:
   fitting the subject's head with a close-fitting skull cap prior to scanning, said skull-cap having a plurality of markers;
   obtaining a plurality of laser camera images of said cap by means of said scanning so that at least one of said markers appears commonly in each adjacent pair of images; and
   using the commonly appearing markers to merge the images in order to obtain the 3-D model of the subject's head.

3. A method as in claim 2 further comprising:
   obtaining the camera images by locating a laser camera above the subject's head so that the camera has an acute look-down angle with respect to the horizontal.

4. A method as in claim 3 wherein the acute angle is about 30 degrees.

5. A method as in claim 2 further comprising:
   determining the subject's line of sight direction; and
   obtaining the camera images by locating the camera at a plurality of positions with respect to the subject's line of sight direction.

6. A method as in claim 5 wherein the positions are at approximately 45 degrees, 135 degrees, 225 degrees, and 315 degrees with respect to the line of sight direction.

7. A method as in claim 5 wherein the camera is located in a fixed position and the images are obtained by rotating the fixture and the subject.

8. A method as in claim 1 wherein the position of the subject's pupils with respect to the fixture is determined by scanning the subject's eyes with the laser while the subject's head is positioned in the fixture.

9. A method as in claim 1 further comprising:
   providing the fixture with a pupil locating assembly comprising a pair of components which can be precisely aligned with respect to the subject's pupils when the head is positioned in the fixture;
   precisely aligning the components with respect to the subject's pupils;
   obtaining laser camera images of the components by scanning surfaces of the components; and
   using the laser camera images of the components to determine the position of the subject's pupils with respect to the 3-D model of the subject's head.

10. A method as in claim 9 wherein the pupil locating assembly further comprises a pair of sights which can be moved laterally to align with respective lines of sight of the subject's eyes, the pair of components being laterally fixed with respect to respective sights and movable fore and aft with respect to said sight, said method further comprising:
    moving said sights laterally so that the lines of sight of said eyes and the interpupillary distance are established.

11. A method as in claim 9 further comprising:
    fitting the subject's head with a close fitting skull cap prior to scanning, wherein the skull cap is provided with at least one anthropometric marker which is fitted over a respective at least one anthropometric point on the subject's head; and
    using the at least one anthropometric marker to align the subject's head within the pupil locating assembly.

12. A method as in claim 1 further comprising:
    manipulating the 3-D model of the subject's head to provide a modified 3-D model having a constant offset from the subject's head;
    providing the liner with an offset inner surface conforming to the modified 3-D model; and
    fitting the offset inner surface with at least one layer in order to provide the inner surface which conforms to the subject's head, the at least one layer having a thickness corresponding to the offset.

13. A method as in claim 12 wherein the at least one layer comprises a layer of comfort foam and a cover.

14. A method as in claim 1 further comprising shaping the outer surface to form cavities between the liner and the helmet shell.

15. An apparatus for determining the precise position of a subject's pupils with respect to a 3-D model of a subject's head, the apparatus comprising:
    a fixture for positioning the subject's head;
    a pupil locating assembly having components which can be moved with respect to the fixture, the components being precisely alignable with respect to the subject's pupils;
    means for obtaining a 3-D model of the subject's head while positioned in the fixture; and
    means for determining the precise position of the components with respect to the fixture, whereby,
    the 3-D model of the subject's head, the position of the subject's head with respect to the fixture, and the position of the components with respect to the fixture can be used to determine the position of the subject's pupils with respect to the 3-D model of the subject's head.

16. An apparatus as in claim 15 wherein the means for providing a 3-D model of the subject's head comprises a laser scanning device which is movable with respect to the fixture in order to obtain laser camera images of the subject's head while positioned in the fixture, whereby the laser camera images can be used to generate the 3-D model of the subject's head.

17. An apparatus as in claim 16 wherein the laser scanning device also serves as the means for determining the precise position of the components with respect to the 3-D model of the subject's head, the components having surfaces which can be imaged by the laser scanning device.

18. An apparatus as in claim 16 further comprising a close-fitting skull cap which can be fitted to the subject's head so that said laser scanning device can obtain camera images of the subject's head with the skull cap fitted.

19. An apparatus as in claim 18 wherein the skull cap is provided with anthropometric markers which can be aligned with anthropometric points on the subject's head, the fixture being provided with anthropometric features which can be aligned with the anthropometric markers on the skull cap in order to align the subject's head with respect to the fixture.

20. An apparatus as in claim 16 wherein the skull cap is provided with markers which can be used to merge overlapping images to form said 3-D model.

21. An apparatus as in claim 15 wherein the fixture comprises a chin support.

22. An apparatus as in claim 15 wherein the components of the pupil locating assembly comprise:
   a pair of corneal locating blocks which are movable fore and aft with respect to said fixture and laterally with respect to each other, each corneal locating block having means for precisely aligning the block with the respective cornea of a subject's eye.

23. An apparatus as in claim 22 wherein the means for aligning with the respective cornea comprises an optical sight with a reticule.

24. An apparatus as in claim 22 wherein the pupil locating assembly comprises a central holding block, the corneal locating blocks being movable fore and aft and laterally with respect to the central holding block.

25. An apparatus as in claim 24 wherein the central holding block is movable vertically with respect to the fixture.

26. An apparatus as in claim 24 further comprising a pair of sighting blocks which are movable laterally with respect to the holding block, each said sighting block carrying a respective sight for establishing the line of sight of a respective eye, whereby the subject's interpupillary distance can be used to determine the separation of the sighting blocks, said corneal locating blocks being movable fore and aft with respect to respective said sighting blocks.

27. An apparatus as in claim 26 wherein the sighting blocks are movable symmetrically with respect to the central holding block by means of a shaft received through the central holding block, the shaft having a right hand thread in one of said sighting blocks and a left hand thread in the other of said sighting blocks.

28. An apparatus as in claim 26 wherein each said corneal locating block is movable fore and aft with respect to the respective sighting block by means of a respective screw.

29. An apparatus as in claim 26 wherein each said sighting block is provided with an anthropometric aligning feature which can be aligned with an anthropometric point on the subject's head, thereby providing means for aligning the subject's head in the fixture.

* * * * *